US012207918B2

(12) United States Patent
Koivisto et al.

(10) Patent No.: US 12,207,918 B2
(45) Date of Patent: Jan. 28, 2025

(54) APPARATUS FOR PRODUCING INFORMATION INDICATIVE OF CARDIAC ABNORMALITY

(71) Applicant: PRECORDIOR OY, Turku (FI)

(72) Inventors: Tero Koivisto, Turku (FI); Mojtaba Jafari Tadi, Turku (FI); Mikko Pänkäälä, Turku (FI); Juuso Blomster, Turku (FI); Juhani Airaksinen, Turku (FI); Antti Saraste, Turku (FI)

(73) Assignee: Precordior Oy, Turku (FI)

( * ) Notice: Subject to any disclaimer, the term of this patent is extended or adjusted under 35 U.S.C. 154(b) by 714 days.

(21) Appl. No.: 17/282,261

(22) PCT Filed: Aug. 8, 2019

(86) PCT No.: PCT/FI2019/050580
§ 371 (c)(1),
(2) Date: Apr. 1, 2021

(87) PCT Pub. No.: WO2020/070374
PCT Pub. Date: Apr. 9, 2020

(65) Prior Publication Data
US 2021/0338108 A1    Nov. 4, 2021

(30) Foreign Application Priority Data

Oct. 1, 2018 (FI) .................................... 20185814

(51) Int. Cl.
*A61B 5/11* (2006.01)
*A61B 5/00* (2006.01)
(52) U.S. Cl.
CPC .......... *A61B 5/1102* (2013.01); *A61B 5/6898* (2013.01); *A61B 5/6823* (2013.01); *A61B 2562/0219* (2013.01)

(58) Field of Classification Search
CPC .......... A61B 2562/0219; A61B 5/1102; A61B 5/6823; A61B 5/6898; A61B 5/7257;
(Continued)

(56) References Cited

U.S. PATENT DOCUMENTS 6,009,349 A    12/1999  Mouchawar
10,492,733 B2  12/2019  Airaksinen et al.
(Continued)

FOREIGN PATENT DOCUMENTS

CN    107979986 A    5/2018
CN    108430327 A    8/2018
(Continued)

OTHER PUBLICATIONS

Office Action issued in Indian Patent Application No. 202127013548 dated Sep. 23, 2022.
(Continued)

*Primary Examiner* — Amanda K Hulbert
(74) *Attorney, Agent, or Firm* — WILSON SONSINI GOODRICH & ROSATI

(57) ABSTRACT

An apparatus for producing information indicative of cardiac abnormality, for example Heart failure with preserved ejection fraction "HFpEF", includes a signal interface for receiving a signal indicative of cardiac motion and a processing system coupled to the signal interface. The processing system is configured to extract, from the signal, temporal portions which belong to diastolic phases of a heart. The processing system is configured to set an output signal of the apparatus to express presence of cardiac abnormality based on a result of a comparison between the indicator quantity and a threshold value.

12 Claims, 4 Drawing Sheets

(58) Field of Classification Search
CPC ..... A61B 5/1116; A61B 5/1128; A61B 5/742; A61B 5/746
See application file for complete search history.

(56) References Cited

U.S. PATENT DOCUMENTS

| | | |
|---|---|---|
| 2008/0319498 A1 | 12/2008 | Hedberg |
| 2012/0004564 A1 | 1/2012 | Dobak, II |
| 2013/0109989 A1 | 5/2013 | Busse et al. |
| 2014/0288442 A1 | 9/2014 | Bombardini |
| 2015/0065894 A1 | 3/2015 | Airaksinen et al. |
| 2015/0366901 A1 | 12/2015 | Chirinos |
| 2018/0020931 A1 | 1/2018 | Shusterman |
| 2018/0035919 A1 | 2/2018 | Koivisto |
| 2018/0043158 A1 | 2/2018 | Thakur |
| 2018/0098709 A1 | 4/2018 | Hirsh |
| 2018/0214030 A1 | 8/2018 | Migeotte |
| 2018/0249962 A1 | 9/2018 | Koivisto et al. |
| 2021/0361190 A1 | 11/2021 | Airaksinen |

FOREIGN PATENT DOCUMENTS

| | | |
|---|---|---|
| CN | 108471987 A | 8/2018 |
| EP | 3135194 A1 | 3/2017 |
| JP | 2015-517842 A | 6/2015 |
| KR | 20160126660 A | 11/2016 |
| WO | 2012/149652 | 11/2012 |
| WO | 2013/121431 | 8/2013 |
| WO | 2017/060569 A1 | 4/2017 |

OTHER PUBLICATIONS

Office Action issued in Japanese Patent Application No. 2021-517794 dated Apr. 4, 2023.

M. Di Rienzo, et al., "Wearable seismocardiography: Towards a beat-by-beat assessment of cardiac mechanics in ambulant subjects", Autonomic Neuroscience: Basic and Clinical, ElSevier, vol. 178, No. 1, May 9, 2013, pp. 50-59 (10 pages).

Kavita Sharma, et al., "Heart Failure With Preserved Ejection Fraction: Mechanisms, Clinical Features, and Therapies", Circulation Research, vol. 115, No. 1, Jun. 20, 2014, pp. 79-96 (18 pages).

Search Report for FI Application No. 20185814 dated Apr. 11, 2019, 2 pages.

International Search Report for PCT/FI2019/050580 dated Oct. 23, 2019, 4 pages.

Written Opinion of the ISA for PCT/FI2019/050580 dated Oct. 23, 2019, 6 pages.

Office Action, issued in European Patent Application No. 19765527.7 dated May 21, 2024.

Office Action, issued in Chinese Patent Application No. 201980055384.8 dated Oct. 28, 2023.

Office Action, issued in Chinese Patent Application No. 201980055384.8 dated Mar. 29, 2024.

APPARATUS FOR PRODUCING INFORMATION INDICATIVE OF CARDIAC ABNORMALITY

This application is the U.S. national phase of International Application No. PCT/FI2019/050580 filed Aug. 8, 2019 which designated the U.S. and claims priority to FI patent application No. 20185814 filed Oct. 1, 2018, the entire contents of each of which are hereby incorporated by reference.

FIELD OF THE DISCLOSURE

The disclosure relates generally to producing information indicative of cardiac abnormality, such as for example Heart failure with preserved ejection fraction "HFpEF". More particularly, the disclosure relates to an apparatus for producing information indicative of cardiac abnormality. Furthermore, the disclosure relates to a computer program for producing information indicative of cardiac abnormality.

BACKGROUND

Abnormalities that may occur in the cardiovascular system, if not diagnosed and appropriately treated and/or remedied, may progressively decrease the ability of the cardiovascular system to maintain a blood flow that meets the needs of a body of an individual especially when the individual encounters physical stress. For example, coronary flow reserve "CFR" is reduced not only because of ischemic heart diseases, but also due to heart failures "HF". Almost half of heart failure patients have a heart failure with preserved ejection fraction "HFpEF". HFpEF patients typically suffer from other comorbidities that may contribute to cardiac and non-cardiac morbidity and mortality. These patients have about same mortality rates as patients having a heart failure with reduced ejection fraction "HFrEF". Patients diagnosed to have the HFpEF have greater concentric hypertrophy, atrial enlargement, and diastolic and vascular stiffness. The pathophysiological symptoms of HFpEF are complex and dependent on numerous factors such as diastolic dysfunction, myocardial ischemia, cardiomyocyte hypertrophy, cardiac inflammation, and endothelial dysfunction.

Currently, methods such as cardiography based on electromagnetic phenomena related to cardiac activity, echocardiography, and cardiography based on cardiac motion are used in the identification and assessment of various cardiac abnormalities. A well-known example of the cardiography based on electromagnetic phenomena related to cardiac activity is the electrocardiography "ECG", and examples of the cardiography based on cardiac motion are gyrocardiography "GCG" and seismocardiography "SCG". The echocardiography is typically based on ultrasound and provides images of sections of the heart and can provide comprehensive information about the structure and function of the heart, but requires expensive equipment and specialised operating personnel. The ECG provides a fairly rapid electrical assessment of the heart, but provides only little information relating to the structure of the heart. The Seismocardiography is a non-invasive accelerometer-based method where precordial vibrations of the heart are measured, while gyrocardiography is a non-invasive gyroscope based method where cardiac angular rotations are measured. In this document, the term "gyroscope" covers sensors of various kinds for measuring angular rotations. For example, the above-mentioned heart failure with reduced ejection fraction "HFrEF" can be relatively straightforwardly detected with ultrasound-based echocardiography. The situation is however more challenging in conjunction with the above-mentioned heart failure with preserved ejection fraction "HFpEF".

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new apparatus for producing information indicative of cardiac abnormality such as for example heart failure with preserved ejection fraction "HFpEF". The apparatus according to the invention comprises a signal interface for receiving a signal indicative of cardiac motion and a processing system coupled to the signal interface. The processing system is configured to:
  extract, from the signal, temporal portions which belong to diastolic phases of a heart,
  form an indicator quantity indicative of energy of the temporal portions belonging to the diastolic phases, and
  set an output signal of the apparatus to express presence of cardiac abnormality based on a result of a comparison between the indicator quantity and a threshold value.

In light of empirical data, the above-mentioned indicator quantity indicative of the energy related to diastolic phases can be used as an indicator of cardiac abnormalities. For example, an increase in the above-mentioned energy means an increased probability of a heart failure with preserved ejection fraction "HFpEF".

The above-mentioned threshold value which is compared to the indicator quantity can be determined based on empirical data gathered from a group of patients and healthy persons. The threshold value is not necessary constant, but the threshold value can be changing according to the individual under consideration, according to time, and/or according to some other factors. It is also possible to construct a series of threshold values where each threshold value represents a specific probability of HFpEF or some other cardiac abnormality.

The apparatus may comprise a sensor system for measuring the signal indicative of cardiac motion. The sensor system may comprise a gyroscope for measuring cardiac angular rotations and/or an accelerometer for measuring cardiac accelerations. It is also possible that the signal interface is capable of receiving the signal from an external device comprising an appropriate sensor system, i.e. it is emphasized that the apparatus does not necessarily comprise means for measuring the signal indicative of cardiovascular motion. The apparatus can be for example a smartphone or another hand-held device comprising a gyroscope and/or an accelerometer. The apparatus can be placed on an individual's chest to measure mechanical signals caused by heart-beats.

In accordance with the invention, there is provided also a new computer program for producing information indicative of cardiac abnormality on the basis of the above-mentioned signal indicative of cardiac motion. The computer program comprises computer executable instructions for controlling a programmable processing system to:

extract, from the signal, temporal portions which belong to diastolic phases of a heart, form an indicator quantity indicative of energy of the temporal portions belonging to the diastolic phases, and set an output signal to express presence of cardiac abnormality based on a result of a comparison between the indicator quantity and a threshold value.

In accordance with the invention, there is provided also a new computer program product. The computer program product comprises a non-volatile computer readable medium, e.g. a compact disc "CD", encoded with a computer program according to the invention.

Various exemplifying and non-limiting embodiments of the invention are described in accompanied dependent claims.

Various exemplifying and non-limiting embodiments of the invention both as to constructions and to methods of operation, together with additional objects and advantages thereof, will be best understood from the following description of specific exemplifying embodiments when read in conjunction with the accompanying drawings.

The verbs "to comprise" and "to include" are used in this document as open limitations that neither exclude nor require the existence of also un-recited features. The features recited in the accompanied dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments of the invention and their advantages are explained in greater detail below with reference to the accompanying drawings, in which.

DESCRIPTION OF EXEMPLIFYING AND NON-LIMITING EMBODIMENTS

The specific examples provided in the description below should not be construed as limiting the scope and/or the applicability of the appended claims. Lists and groups of examples provided in the description are not exhaustive unless otherwise explicitly stated.

Figure 1:
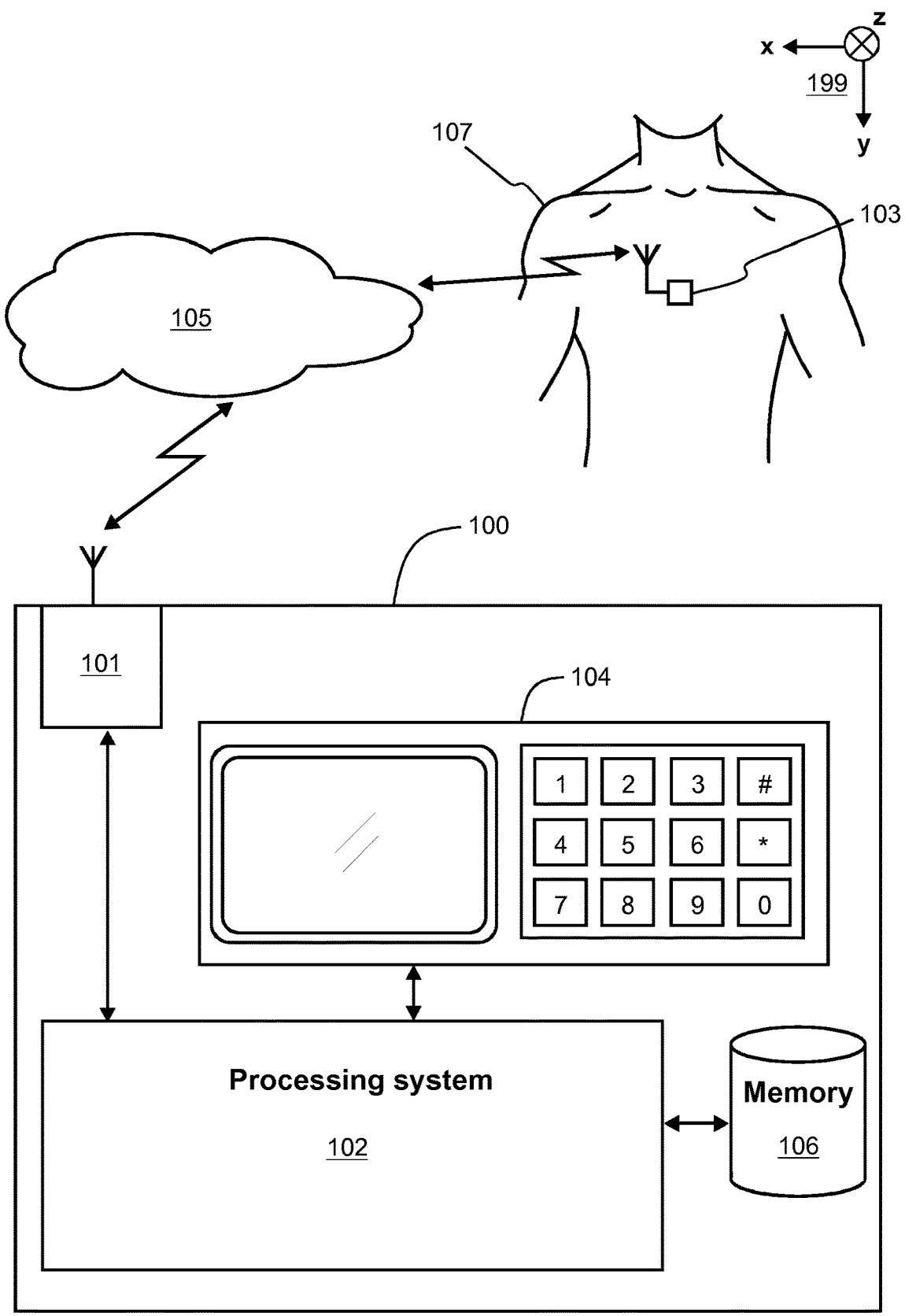
FIG. 1 shows a schematic illustration of an apparatus according to an exemplifying and non-limiting embodiment of the invention for producing information indicative of cardiac abnormality.

FIG. 1 shows a schematic illustration of an apparatus 100 according to an exemplifying and non-limiting embodiment of the invention for producing information indicative of cardiac abnormality such as e.g. a heart failure with preserved ejection fraction "HFpEF". The apparatus comprises a signal interface 101 for receiving a signal indicative of cardiac motion and a processing system 102 coupled to the signal interface 101. The processing system 102 is configured to:

extract, from the signal, temporal portions which belong to diastolic phases of a heart, form an indicator quantity indicative of energy of the temporal portions belonging to the diastolic phases, and set an output signal of the apparatus to express presence of cardiac abnormality based on a result of a comparison between the indicator quantity and a threshold value.

The above-mentioned signal is produced with a sensor system 103 that is responsive to cardiac motion. In the exemplifying situation shown in FIG. 1, the sensor system 103 is placed on the chest of an individual 107. The sensor system 103 may comprise for example a gyroscope, an accelerometer, and/or an inertial measurement unit "IMU" comprising both an accelerometer and a gyroscope. The sensor system 103 can be for example a microelectromechanical system "MEMS". The temporal duration of the signal measured with the sensor system can be, for example but not necessarily, from tens of seconds to hours. The output signal of the apparatus can be for example a message shown on a display screen of a user-interface 104. The temporal portions which belong to the diastolic phases can be recognized and extracted from the signal with suitable known methods that can be based on e.g. known waveform complexes which are related to the systolic phase and to the diastolic phase, respectively.

In the exemplifying case illustrated in FIG. 1, the sensor system 103 is connected to the signal interface 101 via one or more data transfer links each of which can be for example a radio link or a corded link. The data transfer from the sensor system 103 to the signal interface 101 may take place either directly or via a data transfer network 105 such as e.g. a telecommunications network. In the exemplifying case illustrated in FIG. 1, the sensor system 103 is connected to a radio transmitter. It is also possible that the apparatus comprising the processing device 102 is integrated with the sensor system. In this exemplifying case, the signal interface is actually a simple wiring from the sensor system to the processing device. An apparatus comprising an integrated sensor system can be for example a smartphone or another hand-held device which can be placed on the chest of an individual during a measurement phase.

An apparatus according to an exemplifying and non-limiting embodiment of the invention is configured to record the signal indicative of cardiac motion. The recorded signal can be measured within a time window having a fixed temporal start-point and a fixed temporal end-point or within a sliding time window having a fixed temporal length and moving along with elapsing time. The apparatus may comprise an internal memory 106 for recording the signal and/or the apparatus may comprise a data port for connecting to an external memory.

There are numerous ways to form the indicator quantity indicative of the energy related to the diastolic phases of heart-beat periods. In an apparatus according to an exemplifying and non-limiting embodiment of the invention, the processing system 102 is configured to compute the indicator quantity according to the formula:

$$\sum_{i=1}^{N}(x_i^2+y_i^2+z_1^2), \qquad (1)$$

where i is an index increasing with time, and N is the number of samples taken from the signal during the diastolic phases of heart-beat periods. In an exemplifying case where the signal is measured with a three-axis gyroscope, $x_i$ is an $i^{th}$ sample of cardiac rotation with respect to the x-direction of a cartesian coordinate system 199, $y_i$ is an $i^{th}$ sample of cardiac rotation with respect to the y-direction of the cartesian coordinate system 199, and $z_i$ is an $i^{th}$ sample of cardiac rotation with respect to the z-direction of the cartesian coordinate system 199. In an exemplifying case where the signal is measured with a three-axis accelerometer, $x_i$ is an $i^{th}$ sample of acceleration in the x-direction of the cartesian coordinate system 199, $y_i$ is an $i^{th}$ sample of acceleration in the y-direction of the cartesian coordinate system 199, and $z_i$ is an $i^{th}$ sample of acceleration in the z-direction of the cartesian coordinate system 199. It is also possible that the sensor system comprises both a gyroscope and an accelerometer. In this exemplifying case, the processing system 102 can be configured apply the above-presented formula (1) for both the x-, y-, and z-components of the cardiac rotation and the x-, y-, and z-components of the acceleration. The final indicator quantity can be e.g. a weighted sum of the results computed for the cardiac rotation and for the acceleration.

In an apparatus according to an exemplifying and non-limiting embodiment of the invention, the processing system 102 is configured to set the output signal of the apparatus to express presence of a heart failure with preserved ejection fraction "HFpEF" in response to a situation in which the indicator quantity exceeds the threshold value.

In an apparatus according to an exemplifying and non-limiting embodiment of the invention, the processing system 102 is configured to maintain a series of threshold values where each threshold value represents a specific probability of cardiac abnormality e.g. the HFpEF. The processing system 102 is configured to set the output signal of the apparatus to express the probability of cardiac abnormality based on results of comparisons between the indicator quantity and the threshold values.

In an apparatus according to an exemplifying and non-limiting embodiment of the invention, the processing system 102 is configured to extract, from the signal, the temporal portions so that the extracted temporal portions represent end-parts of the diastolic phases. Each end-part may cover at most e.g. 50% or 30% of the corresponding diastolic phase. According to empirical data, the energy of temporal portions of a signal measured with an accelerometer and representing the end-parts of diastolic periods can be used as an indicator of the HFpEF.

The processing system 102 can be implemented for example with one or more processor circuits, each of which can be a programmable processor circuit provided with appropriate software, a dedicated hardware processor such as, for example, an application specific integrated circuit "ASIC", or a configurable hardware processor such as, for example, a field programmable gate array "FPGA". The memory 106 can be implemented for example with one or more memory circuits, each of which can be e.g. a random-access memory "RAM" device.

Figure 2A:
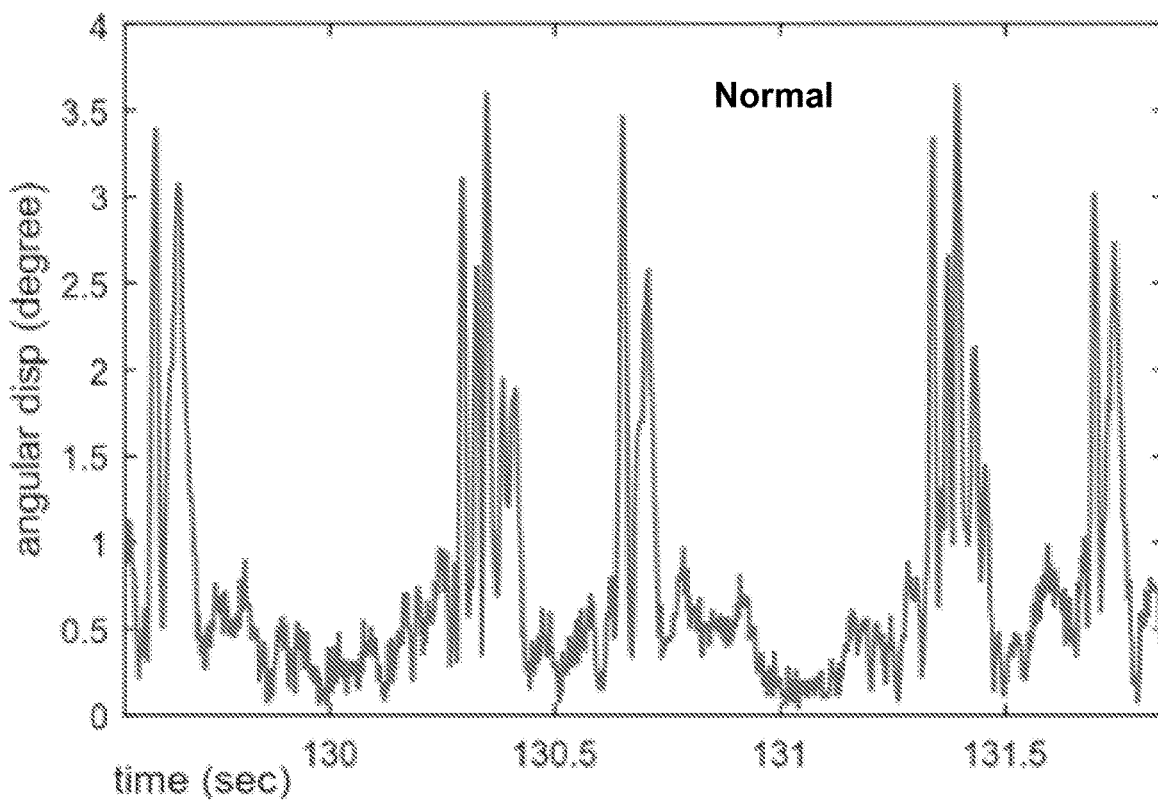
FIG. 2a illustrates a waveform of an exemplifying signal indicative of cardiac rotation in a normal case when an individual under consideration is at rest.

FIG. 2a illustrates the waveform of an exemplifying signal indicative of cardiac rotation in a normal case when an individual under consideration is at rest. In an exemplifying case where the signal is measured with a three-axis gyroscope, the cardiac rotation can be defined as:

$$\sqrt{(x_i^2+y_i^2+z_i^2)}, \qquad (2)$$

where i is an index increasing with time, $x_i$ is an $i^{th}$ sample of the cardiac rotation with respect to the x-direction of the cartesian coordinate system 199 shown in FIG. 1, $y_i$ is an $i^{th}$ sample of the cardiac rotation with respect to the y-direction of the cartesian coordinate system 199, and $z_i$ is an $i^{th}$ sample of the cardiac rotation with respect to the z-direction of the cartesian coordinate system 199.

Figure 2B:
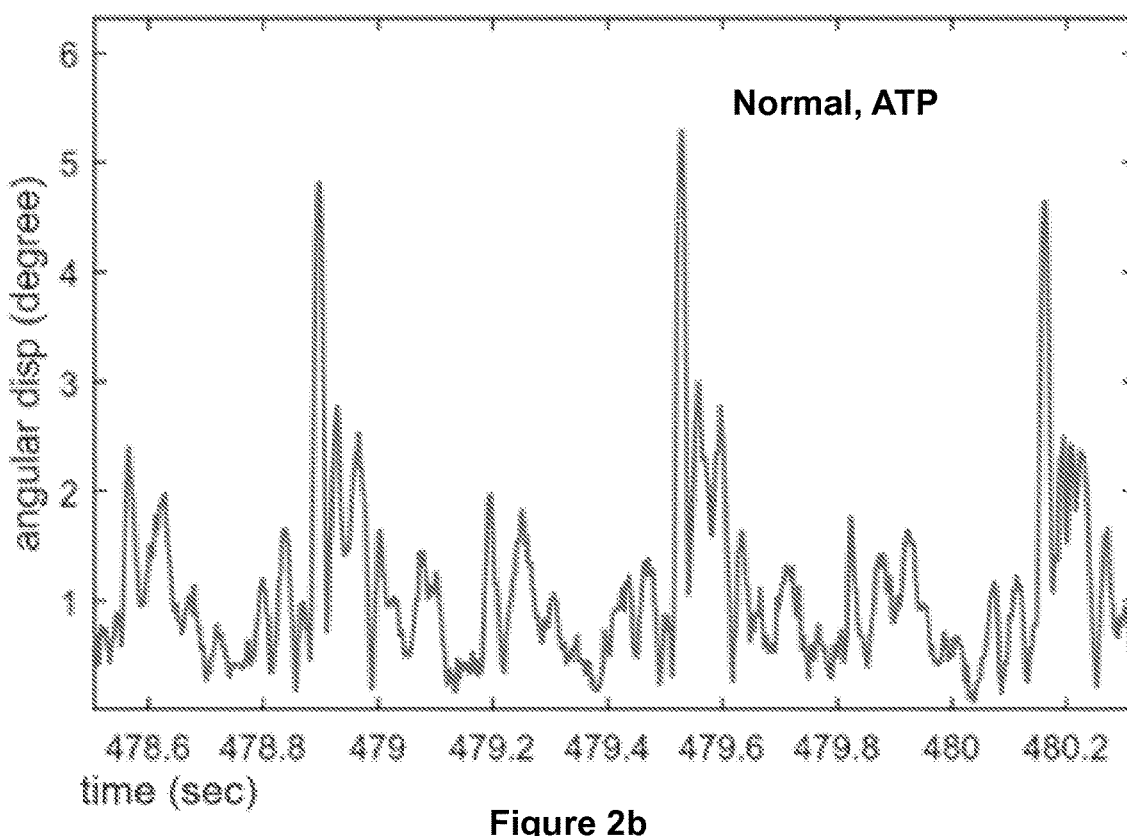
FIG. 2b illustrates a waveform of another exemplifying signal indicative of cardiac rotation measured from the same individual after adenosine triphosphate "ATP" infusion for widening coronary arteries.

FIG. 2b illustrates the waveform of an exemplifying signal indicative of cardiac rotation measured from the same individual after adenosine triphosphate "ATP" infusion for widening coronary arteries.

Figure 3A:
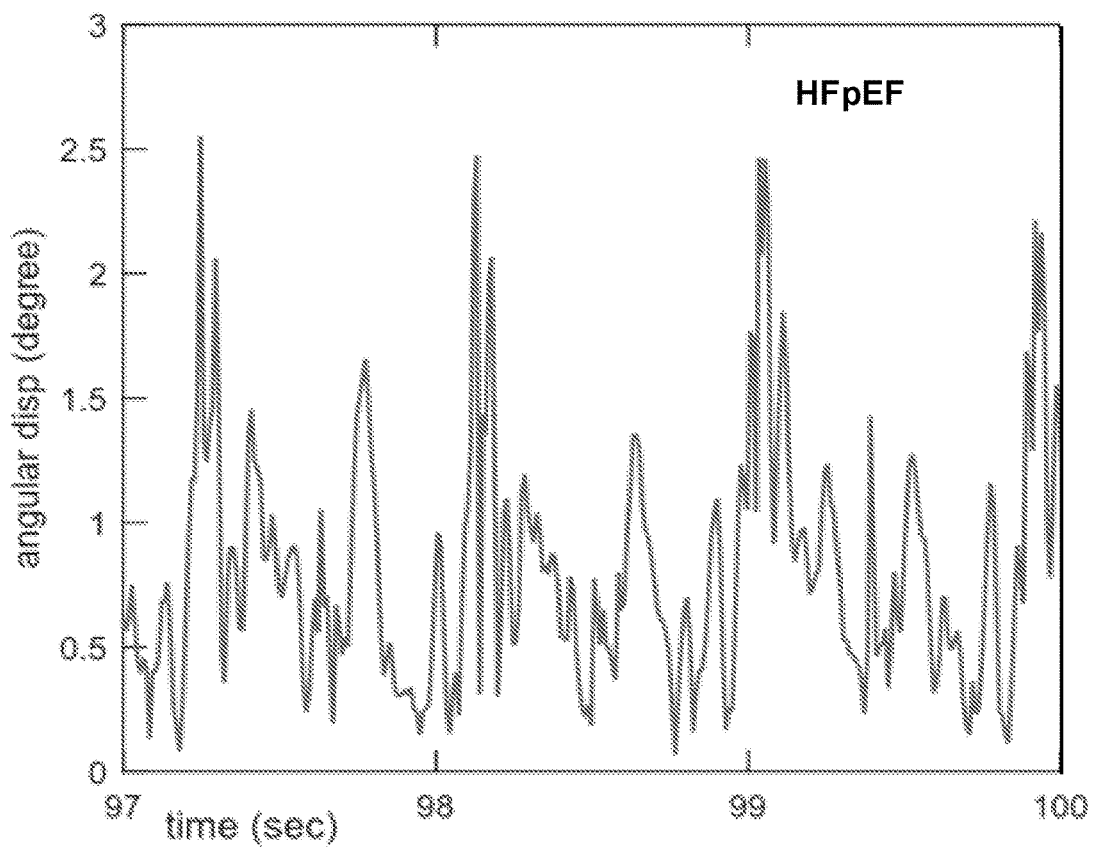
FIG. 3a illustrates a waveform of an exemplifying signal indicative of cardiac rotation in a case of a heart failure with preserved ejection fraction "HFpEF" when an individual under consideration is at rest.
Figure 3B:
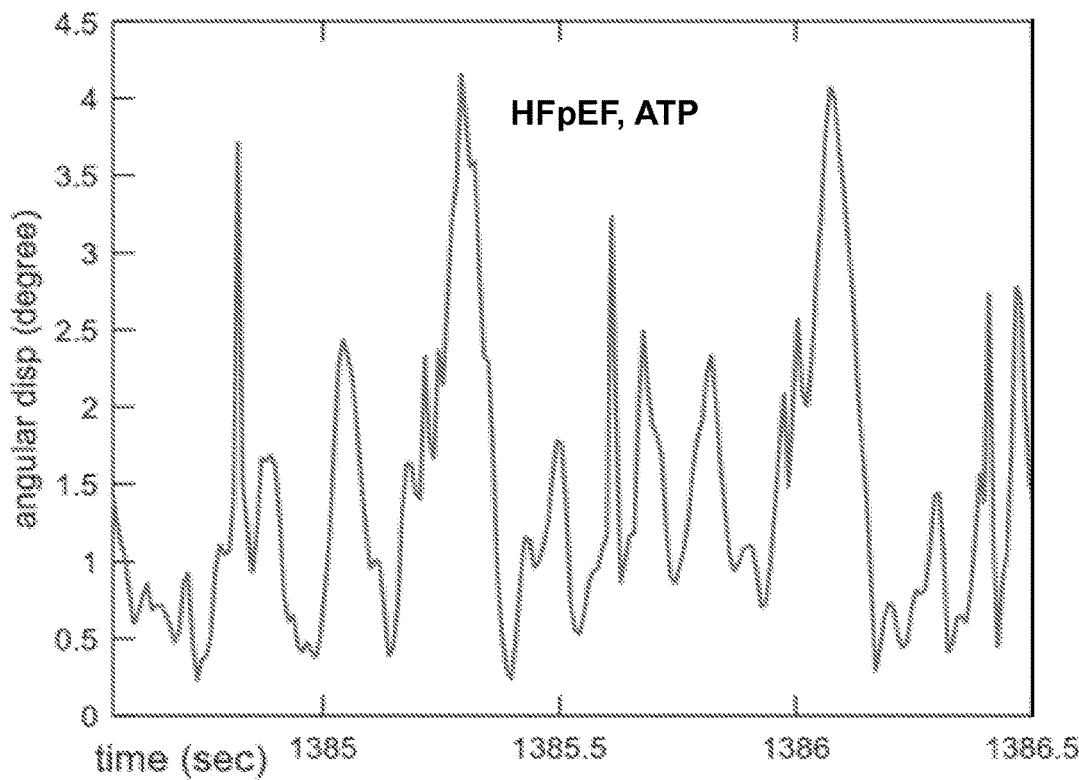
FIG. 3b illustrates a waveform of another exemplifying signal indicative of cardiac rotation measured from the same individual after adenosine triphosphate "ATP" infusion for widening coronary arteries.

FIG. 3a illustrates the waveform of an exemplifying signal indicative of cardiac rotation in a case of a heart failure with preserved ejection fraction "HFpEF" when an individual under consideration is at rest. FIG. 3b illustrates the waveform of an exemplifying signal indicative of cardiac rotation measured from the same individual after adenosine triphosphate "ATP" infusion for widening coronary arteries. As shown by FIGS. 2a, 2b, 3a, and 3b, the energy related to diastolic phases of heart-beat periods is greater in the cases of the HFpEF shown in FIGS. 3a and 3b than in the normal cases shown in FIGS. 2a and 2b.

Figure 4A:
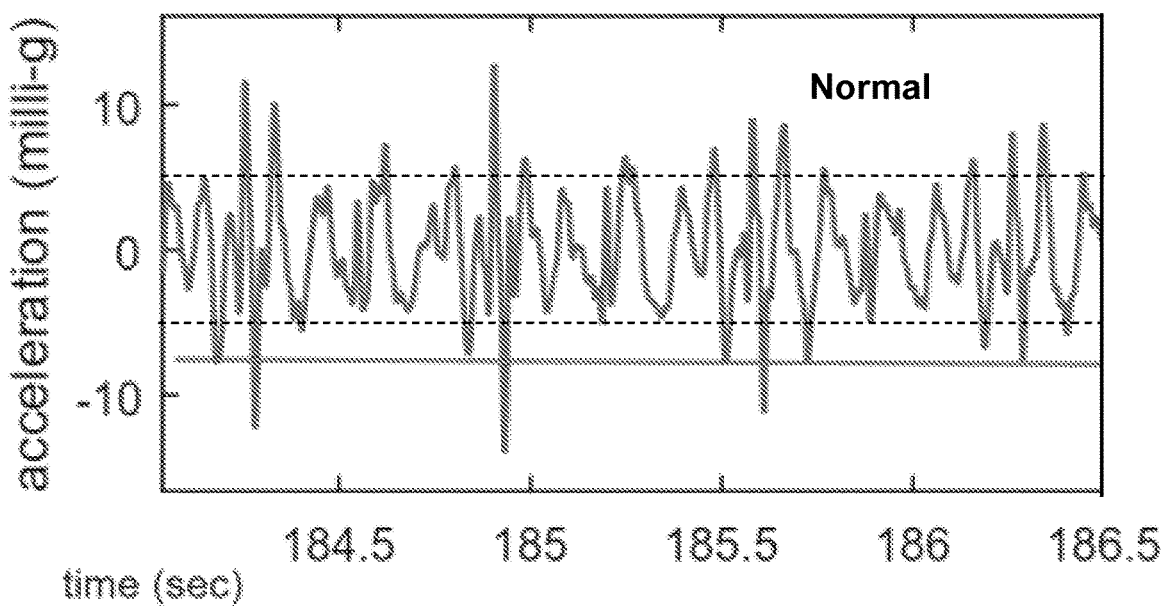
FIG. 4a illustrates a waveform of an exemplifying signal indicative of acceleration in the "through chest"-direction in a normal case when an individual under consideration is at rest.
Figure 4B:
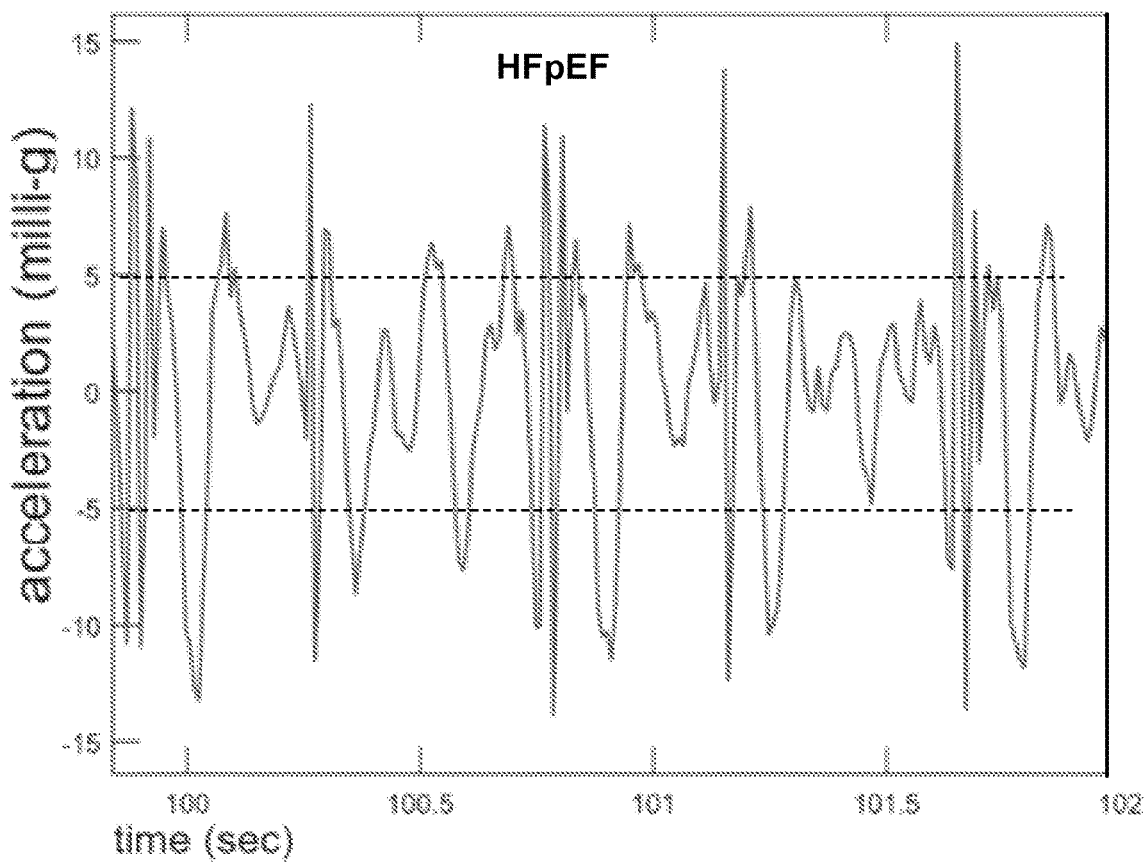
FIG. 4b illustrates a waveform of another exemplifying signal indicative of acceleration in the "through chest"-direction in a case of a heart failure with preserved ejection fraction "HFpEF" when an individual under consideration is at rest.

FIG. 4a illustrates a waveform of an exemplifying signal indicative of acceleration in the "through chest"-direction in a normal case when an individual under consideration is at rest. The through chest"-direction is the z-direction of the cartesian coordinate system 199 shown in FIG. 1. FIG. 4b illustrates a waveform of an exemplifying signal indicative of acceleration in the "through chest"-direction in a case of a heart failure with preserved ejection fraction "HFpEF" when an individual under consideration is at rest. As shown by FIGS. 4a and 4b, the energy related to diastolic phases of heart-beat periods is greater in the case of the HFpEF than in the normal case.

A computer program according to an exemplifying and non-limiting embodiment of the invention comprises software modules for producing information indicative of cardiac abnormality, e.g. HFpEF, on the basis of a signal indicative of cardiac motion. The software modules comprise computer executable instructions for controlling a programmable processing system to:

extract, from the signal, temporal portions which belong to diastolic phases of a heart, form an indicator quantity indicative of energy of the temporal portions belonging to the diastolic phases, and set an output signal to express presence of cardiac abnormality based on a result of a comparison between the indicator quantity and a threshold value.

In a computer program according to an exemplifying and non-limiting embodiment of the invention, the software modules comprise computer executable instructions for controlling the programmable processing system to compute the indicator quantity according to the above-presented formula (1).

In a computer program according to an exemplifying and non-limiting embodiment of the invention, the software modules comprise computer executable instructions for controlling the programmable processing system to extract, from the signal, the temporal portions so that the extracted temporal portions represent end-parts of the diastolic phases, each end-part covering at most e.g. 50% or 30% of the corresponding diastolic phase.

In a computer program according to an exemplifying and non-limiting embodiment of the invention, the software modules comprise computer executable instructions for controlling the programmable processing system to set the output signal to express presence of the HFpEF in response to a situation in which the indicator quantity exceeds the threshold value.

The software modules can be e.g. subroutines or functions implemented with a suitable programming language and with a compiler suitable for the programming language and for the programmable processing system under consideration. It is worth noting that also a source code corresponding to a suitable programming language represents the computer executable software modules because the source code contains the information needed for controlling the programmable processing system to carry out the above-presented actions and compiling changes only the format of the information. Furthermore, it is also possible that the programmable processing system is provided with an interpreter so that a source code implemented with a suitable programming language does not need to be compiled prior to running.

A computer program product according to an exemplifying and non-limiting embodiment of the invention comprises a computer readable medium, e.g. a compact disc ("CD"), encoded with a computer program according to an embodiment of invention.

A signal according to an exemplifying and non-limiting embodiment of the invention is encoded to carry information defining a computer program according to an embodiment of invention.

The specific examples provided in the description given above should not be construed as limiting the scope and/or the applicability of the appended claims. Lists and groups of examples provided in the description given above are not exhaustive unless otherwise explicitly stated.

What is claimed is:

1. An apparatus comprising:
    a signal interface for receiving a signal indicative of cardiac motion and measured with one or more of following: a gyroscope for measuring cardiac angular rotations or an accelerometer for measuring cardiac accelerations, and
    a processing system coupled to the signal interface, wherein the processing system is configured to:
    extract, from the signal, temporal portions which belong to diastolic phases of a heart so that the extracted temporal portions represent end-parts of the diastolic phases, each end-part covering at most 50% of the corresponding diastolic phase,
    form an indicator quantity indicative of energy of the temporal portions belonging to the diastolic phases, and
    set an output signal of the apparatus to express presence of a heart failure with preserved ejection fraction "HFpEF" in response to a situation in which the indicator quantity exceeds a threshold value.

2. The apparatus according to claim 1, wherein the apparatus comprises a sensor system for producing the signal indicative of the cardiac motion.

3. The apparatus according to claim 2, wherein the sensor system comprises the gyroscope for measuring the cardiac angular rotations.

4. The apparatus according to claim 3, wherein the sensor system comprises the accelerometer for measuring the cardiac accelerations.

5. The apparatus according to claim 3, wherein the processing system is configured to compute the indicator quantity according to the formula:

$$\sum_{i=1}^{N}(x_i^2 + y_i^2 + z_i^2),$$

where i is an index increasing with time, N is a number of samples of the temporal portions belonging to the diastolic phases, $x_i$ is an $i^{th}$ sample of cardiac rotation with respect to, or acceleration in, an x-direction of a cartesian coordinate system (199), $y_i$ is an $i^{th}$ sample of cardiac rotation with respect to, or acceleration in, a y-direction of the cartesian coordinate system, and $z_i$ is an $i^{th}$ sample of cardiac rotation with respect to, or acceleration in, a z-direction of the cartesian coordinate system.

6. The apparatus according to claim 2, wherein the sensor system comprises the accelerometer for measuring the cardiac accelerations.

7. The apparatus according to claim 6, wherein the processing system is configured to compute the indicator quantity according to the formula:

$$\sum_{i=1}^{N}(x_i^2 + y_i^2 + z_i^2),$$

where i is an index increasing with time, N is a number of samples of the temporal portions belonging to the diastolic phases, $x_i$ is an $i^{th}$ sample of cardiac rotation with respect to, or acceleration in, an x-direction of a cartesian coordinate system (199), $y_i$ is an $i^{th}$ sample of cardiac rotation with respect to, or acceleration in, a y-direction of the cartesian coordinate system, and $z_i$ is an $i^{th}$ sample of cardiac rotation with respect to, or acceleration in, a z-direction of the cartesian coordinate system.

8. The apparatus according to claim 2, wherein the processing system is configured to compute the indicator quantity according to the formula:

$$\sum_{i=1}^{N}(x_i^2 + y_i^2 + z_i^2),$$

where i is an index increasing with time, N is a number of samples of the temporal portions belonging to the diastolic phases, $x_i$ is an $i^{th}$ sample of cardiac rotation with respect to, or acceleration in, an x-direction of a cartesian coordinate system (199), $y_i$ is an $i^{th}$ sample of cardiac rotation with respect to, or acceleration in, a y-direction of the cartesian coordinate system, and $z_i$ is an $i^{th}$ sample of cardiac rotation with respect to, or acceleration in, a z-direction of the cartesian coordinate system.

9. The apparatus according to claim 1, wherein the processing system is configured to compute the indicator quantity according to the formula:

$$\sum_{i=1}^{N} (x_i^2 + y_i^2 + z_i^2),$$

where i is an index increasing with time, N is a number of samples of the temporal portions belonging to the diastolic phases, $x_i$ is an $i^{th}$ sample of cardiac rotation with respect to, or acceleration in, an x-direction of a cartesian coordinate system (199), $y_i$ is an $i^{th}$ sample of cardiac rotation with respect to, or acceleration in, a y-direction of the cartesian coordinate system, and $z_i$ is an $i^{th}$ sample of cardiac rotation with respect to, or acceleration in, a z-direction of the cartesian coordinate system.

10. A non-transitory computer readable medium on which is stored a computer program for controlling a programmable processing system to process a signal indicative of cardiac motion and measured with one or more of following: a gyroscope for measuring cardiac angular rotations or an accelerometer for measuring cardiac accelerations, the computer program comprising computer executable instructions that, when executed by the programmable processing system, causes the programmable processing system to:

extract, from the signal, temporal portions which belong to diastolic phases of a heart so that the extracted temporal portions represent end-parts of the diastolic phases, each end-part covering at most 50% of the corresponding diastolic phase, form an indicator quantity indicative of energy of the temporal portions belonging to the diastolic phases, and set an output signal to express presence of a heart failure with preserved ejection fraction "HFpEF" in response to a situation in which the indicator quantity exceeds a threshold value.

11. The non-transitory computer readable medium according to claim 10, wherein the computer program comprises computer executable instructions for controlling the programmable processing system to compute the indicator quantity according to the formula:

$$\sum_{i=1}^{N} (x_i^2 + y_i^2 + z_i^2),$$

where i is an index increasing with time, N is a number of samples of the temporal portions belonging to the diastolic phases, $x_i$ is an $i^{th}$ sample of cardiac rotation with respect to, or acceleration in, an x-direction of a cartesian coordinate system (199), $y_i$ is an $i^{th}$ sample of cardiac rotation with respect to, or acceleration in, a y-direction of the cartesian coordinate system, and $z_i$ is an $i^{th}$ sample of cardiac rotation with respect to, or acceleration in, a z-direction of the cartesian coordinate system.

12. The non-transitory computer readable medium according to claim 11, wherein the computer program comprises computer executable instructions for controlling the programmable processing system to extract, from the signal, the temporal portions so that the extracted temporal portions represent end-parts of the diastolic phases, each end-part covering at most 50% of the corresponding diastolic phase.

* * * * *